United States Patent
Wenz

(10) Patent No.: US 7,273,523 B2
(45) Date of Patent: Sep. 25, 2007

(54) STRONTIUM-APATITE-CEMENT-PREPARATIONS, CEMENTS FORMED THEREFROM, AND USES THEREOF

(75) Inventor: Robert Wenz, Wollstadt (DE)

(73) Assignee: Kyphon Inc., Sunnyvale, CA (US)

( * ) Notice: Subject to any disclaimer, the term of this patent is extended or adjusted under 35 U.S.C. 154(b) by 288 days.

(21) Appl. No.: 11/006,326

(22) Filed: Dec. 6, 2004

(65) Prior Publication Data

US 2005/0142211 A1   Jun. 30, 2005

Related U.S. Application Data

(63) Continuation-in-part of application No. PCT/EP03/05059, filed on May 14, 2003.

(30) Foreign Application Priority Data

Jun. 7, 2002   (DE) ................. 102 25 420

(51) Int. Cl.
*A61L 24/02*   (2006.01)
*A61L 27/12*   (2006.01)

(52) U.S. Cl. .............. 106/690; 106/691; 424/603; 623/23.62

(58) Field of Classification Search ........... 106/690, 106/691; 424/603; 623/23.62
See application file for complete search history.

(56) References Cited

U.S. PATENT DOCUMENTS 4,518,430 A   5/1985   Brown et al.
4,612,053 A   9/1986   Brown et al.
4,959,104 A *  9/1990  Iino et al. ............... 106/691
5,149,368 A   9/1992   Liu et al.

FOREIGN PATENT DOCUMENTS

EP   0835668 A1   4/1998
WO   WO92/02478 A1   2/1992
WO   WO96/14265 A1   5/1996

OTHER PUBLICATIONS

Brown, Walter E. et al.; "A new calcium phosphate, water-setting cement"; 1986, *Chem. Res. Prog.*, pp. 352-379.

* cited by examiner

*Primary Examiner*—C. Melissa Koslow
(74) *Attorney, Agent, or Firm*—Townsend and Townsend and Crew LLP

(57) ABSTRACT

Calcium-strontium-hydroxyphosphate (strontium-apatite-) cement preparations are described, comprising a powder mixture, which contains molar quantities of the components calcium (Ca), strontium (Sr) and phosphate (P) in the mixture in the ranges $1.00 < Ca/P \leq 1.50$ and $0 < Sr/P < 1.5$, together with an alkali salt or an ammonium salt of phosphoric acid, and with water and/or an aqueous solution. The powder mixture particularly contains, as the Ca-component, $Ca_3(PO_4)_2$ (TCP), and as the Sr-component $SrHPO_4$ and/or $Sr_3(PO_4)_2$ and optionally additional $SrCO_3$. As the aqueous mixing solution for the formation of the strontium-apatite cement, an aqueous solution of an alkali salt or an ammonium salt of the phosphoric acid is suitable.

31 Claims, No Drawings

STRONTIUM-APATITE-CEMENT-PREPARATIONS, CEMENTS FORMED THEREFROM, AND USES THEREOF

CROSS-REFERENCES TO RELATED APPLICATIONS

This application is a continuation-in-part of PCT/EP03/05059, which designated the United States, filed on May 14, 2003, which claimed the benefit of German application Number 10225420.6, filed on Jun. 7, 2002, the full disclosures of which are incorporated herein by reference.

BACKGROUND OF THE INVENTION

The invention relates to calcium-strontium-hydroxyphosphate-(strontium-apatite-) cement preparations, which contain calcium and strontium, and to uses thereof. The invention further relates to strontium-apatite cements, which are formed from these cement preparations, and to a process applied for their manufacture. The strontium-apatite is well suitable for medical purposes, in particular as bone substitute materials, with specific suitability for filling bone defects caused by osteoporosis.

The human and animal hard tissue essentially consists of hydroxyapatite, wherein there is mostly no stoichiometric hydroxyapatite, but an apatite structure, in which sodium- (Na), potassium- (K), magnesium- (Mg) and strontium- (Sr) salts are further incorporated.

In addition, carbonate, that is incorporated into the apatite structure by substituting phosphate groups, is further incorporated into the hard tissue.

Physiologically occurring apatite is nanocrystalline, illustrated in the X-ray diffractogram in the form of a band broadening, which does not allow an exact allocation of the apatite structures, as it is rather a superposition of single peaks.

Calcium phosphates are biocompatible and osteoconductive, which means that newly formed bone tissue deposits directly thereon. In addition, they are resorbable, because they are recognized as body-consistent (i.e., the body recognizes them as part of itself) and can be catabolized by specific bone-resorbing cells such as osteoclasts, within the framework of natural bone metabolism and restructuring. During such restructuring processes, calcium phosphates can be catabolized and substituted by endogenous bones.

Calcium phosphate ceramics have been on the market since about 1970. They are predominantly incorporated into the human and animal body in the form of pre-made molded bodies or as granules. These materials proved to be effective in clinical applications, however, they can be incorporated only rarely into defects in a force-fit manner, since the defects are mostly irregular. Failure to provide a force-fit incorporation, however, often results in a washing-out of the granules, or in an in-growth of connective tissue into the defects. This subsequently leads to a failure of augmentation.

Calcium phosphate ceramics are predominantly prepared from hydroxyapatite, whereby these ceramics are not resorbable, or from bi-phasic calcium phosphate ceramics, which consist of varying proportions of β-tricalcium phosphate (β-TCP) and hydroxyapatite and which may be resorbed due to the resorbability of the β-tricalcium phosphate, corresponding to its mass proportion.

Calcium phosphate cements have been mentioned in the literature since 1985. They have advantages over ceramics, because they can be incorporated force-fit into the body (W. E. Brown and L. C. Chow, "A new calcium phosphate, water-setting cement", *Chem. Res. Prog.* (1986) 352-379; U.S. Pat. No. 4,612,053; U.S. Pat. No. 5,149,368; U.S. Pat. No. 4,518,430; WO96/14265; EP0835668 A1). These cements are characterized by a calcium/phosphate (Ca/P) ratio of $\geq 1.5$.

By adding carbonate, this ratio can be increased even further. There are contradictory reports about the resorbability of these materials, because such cements can not be resorbed, if the reaction product is hydroxyapatite. Or, if the reaction product is calcium-deficient hydroxyapatite (CDHA), it is resorbable by osteoclasts and can be substituted with new bone by means of osteoblasts. However, the resorption rate is then not predictable, because the resorption is dependent on the cellular activity of the recipient, the local blood flow rate, and the location of the implant.

Such cements have already been successfully introduced into the market (BoneSource® cement, Norian® SRS® cement, Biobon® cement, Calcibon® cement). A main point of criticism from the user's view, however, is still the unpredictable resorbability. The market demands a product, which ensures a high mechanical stability, and which is eventually completely resorbed. After a certain period of time, the product should be substituted with endogenous bone material. Thus, many manufacturers add soluble minerals such as $CaHPO_4$, $CaSO_4$, $CaCO_3$ or β-TCP to the bone substitute materials, in order to enhance the resorption rate in addition to the passive solubility. However, this solves the problem only partially, because the main component still remains only slightly resorbable or not at all resorbable.

The cement resorption, which is essentially controlled by cellular phenomena, follows the rules of Wolff's Law. Wolff's Law describes the steady bone restructuring conditions, and its main assertion is that bone remains only at locations where it is indeed required from a bio-mechanical point of view. From this assertion, it follows that the pressure strength of an artificial bone substitute material should be directed by that of trabecular bone.

This means that a pressure strength of >40 MPa is not desirable at all, because otherwise a certain "stress-shielding" is generated by the cement, which loosens up the bone structure of the adjacent implant bearing due to the higher strength of the cement. Thereby, the place of the lowest bio-mechanical strength of the cement is shifted to the periphery of the implant bearing, which is not desirable.

The main use of bone substitute materials lies in the filling of metaphysic bone defects and of vertebral bodies. These defects mainly occur during osteoporosis. Osteoporosis is a systemic disease of the whole organism, which is essentially expressed by an imbalance of the bone metabolism. Here, the anabolic and catabolic bone restructuring processes are reversed, and more bone material is decomposed by an osteoclastic activity, than is grown by the osteoblastic activity. Attempts to control this imbalance of bone decomposition rate to bone growth rate have been to deliver various systemically effective substances. These include, inter alia, bisphosphonates and hormone preparations, which however threaten the whole organism. In this respect, a bone substitute material that would be desirable is characterized by not only representing a bone substitute substance or filler, but a material that acts upon the surrounding bone cells in such a way that it reverses the metabolic processes, so that the excessive osteoclastic activity itself is attenuated by the bone substitute material and the osteoblastic activity (the in-growth of bones) is stimulated. The aim is to avoid the development that, once a bone substitute material is incorporated through the osteoblastic activity, it is again rapidly decomposed by the increased osteoclastic activity, without the ability of building up new bone at the same time due to the attenuation of osteoblastic activity caused by osteoporosis.

These problems are not solved when considering the present state of the art. In WO92/02478 A1 a calcium phosphate cement containing strontium ions in the form of $SrCO_3$ is disclosed, however, the strontium carbonate is only used for influencing the expansion properties of the cement which, as a main component, consists of magnesium ammonium phosphate. In addition, this strontium carbonate is dissolved rapidly out of the cement due to its potential solubility, so that no protracting effect can originate therefrom, and thereby the bone metabolism cannot be influenced.

It would therefore be desirable to provide a material, which is particularly suitable as a bone substitute material, particularly for osteoporotic bone.

BRIEF SUMMARY OF THE INVENTION

Cement preparations according to the invention comprise calcium and strontium ions. The calcium and strontium ions can be incorporated into the preparations as phosphates or hydrogenphosphates, or optionally carbonates. Natural sources (e.g., calcium phosphates) may not be pure and may contain contaminating trace amounts of magnesium. In the present invention, however, magnesium ions are preferably absent or present only in insignificant amounts, such as unavoidable traces (i.e., magnesium ions are of insufficient quantity to substantially inhibit the formation of a strontium-apatite structure).

Due to their composition, the cement preparations of the present invention, and the hardened strontium-apatite materials resulting therefrom, can provide a prolonged release of strontium ions. It is thus possible to improve bone metabolism in osteoporotic bones, particularly by generating anabolic activity of the bone metabolism in the osteoporotic bone. A permanent stimulation of the osteoblastic activity may be achieved in osteoporotic bone, while at the same time the osteoclastic activity (which is elevated in osteoporotic bone) is inhibited.

The present invention further provides a cement system for filling bone defects in a form-fit manner where the cement preparations are hardenable not only at room temperature, but also at body temperature, and are workable by the user for a sufficiently long period. After full hardening, cement preparations according to the invention will have sufficiently high pressure strength in the human or animal body. The calcium-strontium-hydroxyphosphate (strontium-apatite) formed from the cement preparation is nanocrystalline and achieves its maximal strength in a period of a few hours up to a few days.

The cement preparations of the invention may, depending on the biological environment, be biologically degradable or resorbable within the body. The materials according to the invention exhibit good cohesion ability when contacted with body fluids. The materials according to the invention will also have higher water solubility than calcium-deficient hydroxyapatite, such that the favorable solubility promotes replacement of endogenous bone.

Thus, the materials provided by the present invention are suitable not only for closing bone defects, but also for promoting anabolic activity in the bone, and thus can contribute actively to the bone anabolism.

DETAILED DESCRIPTION OF THE INVENTION

The cement preparations of the present invention comprise a powder mixture having a molar calcium-to-phosphate (Ca/P) ratio in the range from about 1 to about 1.5 and a molar strontium-to-phosphate (Sr/P) ratio which does not exceed (i.e., not greater than about) 1.5. The molar Sr/P ratio is preferably at least 0.2 and further preferably at least 0.5. In a preferred embodiment, the phosphate is orthophosphate.

The cement preparation according to the invention can be determined by the chemical composition of the starting components for the formation of the strontium-apatite cement and contains, as minimum components in the powder mixture, at least $SrHPO_4$ and/or $Sr_3(PO_4)_2$, and optionally additional $SrCO_3$ besides $Ca_3(PO_4)_2$ (TCP), which may be present as α- and/or β-TCP.

The subsequent description relates to both aspects of the invention.

The alkali salt or ammonium salt of the phosphoric acid may be present, as starting material of the preparation, separately from the powder mixture and the water and/or the aqueous solution. In one embodiment of the invention, the phosphoric acid is orthophosphoric acid. The salt may be present in the form of its aqueous solution which is mixed as mixing liquid (i.e., aqueous component) with the dry powder mixture (i.e., powder mixture component) for the formation of the cement. For controlling the reaction rate, additional alkali salt or ammonium salt may be present in dry form in the powder mixture. For this, the powder mixture preferably contains in addition $NaH_2PO_4$ and/or $Na_2HPO_4$, $KH_2PO_4$ and/or $K_2HPO_4$ or combinations of the mentioned Na- and K-salts of the orthophosphoric acid.

As an alkali salt for the aqueous solution of the mixing liquid, a Na- and/or a K-salt of the orthophosphoric acid is particularly suitable, especially the primary or the secondary salts and particularly their combinations. In one embodiment, the alkali salt of the orthophosphoric acid includes, but is not limited to, a primary potassium salt ($KH_2PO_4$), a secondary potassium salt ($K_2HPO_4$) of the orthophosphoric acid and a mixture thereof, and a primary sodium salt ($NaH_2PO_4$), a secondary sodium salt ($Na_2HPO_4$) of the orthophosphoric acid and a mixture thereof, and combinations of the mentioned potassium and sodium salts. As an ammonium salt for the aqueous solution of the mixing liquid, $(NH_4)_2HPO_4$ is particularly suitable.

In one embodiment, for the strontium ions to be incorporated into the strontium-apatite structure in a favorable manner, the strontium is present in the powder mixture advantageously as strontium phosphate ($Sr_3(PO_4)_2$), or as strontium hydrogenphosphate ($SrHPO_4$), or a mixture thereof. The amount of $SrHPO_4$ and/or $Sr_3(PO_4)_2$ in the powder mixture is preferably more than about 10 wt.-% (weight percent) and up to about 60 wt.-%. In another embodiment, more than about 15 wt.-%, particularly more than about 20 wt.-% thereof is contained.

The optionally additional incorporated $SrCO_3$ in the powder mixture may be present in an amount of, for example, about 0.01 wt.-% to about 10 wt.-%.

The powder mixture may contain, as desired, additional suitable substances, e.g., metal carbonates, Ca-, Mg-, Sr-, Na-, K-sulfates, Ca-, Na-, K-phosphates, Ca-, Na-, K-hydrogen-phosphates as well as their oxides and/or hydroxides.

For the preparation of the strontium-apatite cement, the powder components described above are mixed with the above described aqueous component (the mixing liquid) and this mixture is subsequently allowed to be hardened, so that the strontium-apatite is formed as reaction product. Here, the powder mixture may be brought to hardening both by alkali solutions, which contain $(NH_4)_2HPO_4$, $K_2HPO_4$ and/or $Na_2HPO_4$, as well as by acid solutions, which contain NaH$_2$PO$_4$ and/or KH$_2$PO$_4$, or by means of suitable mixed solutions of the mentioned primary and secondary orthophosphates. The aqueous solution preferably has a pH value in the range of about 5 to about 12.

After mixing, a paste is usually formed. This paste can be filled into a mold, whereby after hardening of the paste conforming to the mold matrix, defined molded bodies may be prepared. Here, the viscosity and/or the consistency of the mixture can be adjusted in such a manner that it may not only be incorporated by tools into defects in the form of a paste, but may also be injected.

Embodiments of the cement preparation and the strontium-apatite cement of the present invention may be used for medical purposes and are particularly suitable as bone substitute material, as bone filler, as bone cement, as bone adhesive, and above all as a therapeutic agent for the treatment of osteoporosis.

The cement preparation and the strontium-apatite cement according to the invention are additionally suitable as supporting material for drugs of biological or pharmaceutical origin. For this, the preparation additionally contains, in the powder component and/or the aqueous liquid component, a pharmacological and/or biologically active substance, such as an antibiotic, a cytostatic agent, an analgetic agent (i.e., analgesic), a disinfectant, a growth factor, a protein or a biopolymer, or combinations of the mentioned effective substances. The use of a drug from the group of gentamicin, tobramycin, clindamycin, vancomycin, a drug from the transforming growth factor beta (TGF-β) series, or a drug from the series of bone morphogenetic proteins (BMPs), or combinations of the mentioned drugs are particularly suitable.

In one embodiment, the preparation additionally contains, in the powder component, a substance in the form of granular particles which dissolves in the aqueous liquid component, e.g., salts, sugars, or synthetic, hydrolytically decomposable polymers. These granular particles, which are used, e.g., in a grain size of 10 to 300 µm, then generate a pore system after the mixing and during the hardening process, whereby the surface area is increased and the resorption performance is accelerated.

The invention is subsequently explained in further detail by means of non-limiting examples.

EXAMPLES

In the Examples, the Following Abbreviations are Used

| | |
|---|---|
| M = | powder mixture |
| L = | liquid |
| L/M = | liquid/powder-ratio in ml/g |
| $t_i$ = | initial hardening time (according to ASTM C266-89) |
| $t_f$ = | final hardening time (according to ASTM C266-89) |
| $C_s$(xh/yd) = | pressure strength in MPa after a storage of x hours/y days in 37° C. warm 0.7% sodium chloride salt solution |
| MPa = | mega Pascal |

Preparation of strontium-apatite cement preparations and cements formed thereof:

As indicated in the following examples 1 to 7, after weighing all constituents, the powder components M were homogenously ground in a ball mill and subsequently mixed with an aqueous solution L in the indicated ratio. After the lapse of a certain hardening period, the respective pressure strength was determined.

Example 1

M=65 g Ca$_3$(PO$_4$)$_2$+16 g Sr$_3$(PO$_4$)$_2$
L=3.5 M(NH$_4$)$_2$HPO$_4$
L/M=0.40
$C_s$(48 h)=30 MPa
$C_s$(10 d)=43.8 MPa

Example 2

M=65 g Ca$_3$(PO$_4$)$_2$+16 g Sr$_3$(PO$_4$)$_2$
L=4% Na$_2$HPO$_4$
L/M=0.35
$t_i$=13'30"(13 minutes and 30 seconds)

Example 3

M=65 g Ca$_3$(PO$_4$)$_2$+16 g Sr$_3$(PO$_4$)$_2$+3 g SrCO$_3$
L=3,5 M(NH$_4$)$_2$HPO$_4$
L/M=0.40
$C_s$(10 d)=46.4 MPa

Example 4

M=60 g Ca$_3$(PO$_4$)$_2$+10 g Sr$_3$(PO$_4$)$_2$+10 g SrHPO$_4$+3 g SrCO$_3$
L=3M K$_2$HPO$_4$/1M KH$_2$PO$_4$
L/M=0.40
$C_s$(2 h)=3.8 MPa
$C_s$(18 h)=26.4 MPa

Example 5

M=65 g Ca$_3$(PO$_4$)$_2$+16 g SrHPO$_4$+3 g SrCO$_3$
L=3M K$_2$HPO$_4$/1M KH$_2$PO$_4$
L/M=0.30
$C_s$(5 h)=18.4 MPa

Example 6

M=65 g Ca$_3$(PO$_4$)$_2$+12 g Sr$_3$(PO$_4$)$_2$ +14 g SrHPO$_4$+3 g SrCO$_3$
L=3.2M(NH$_4$)$_2$HPO$_4$
L/M=0.35
$C_s$(5 h)=13.0 MPa

Example 7

M=30 g Ca$_3$(PO$_4$)$_2$+10 g Sr$_3$(PO$_4$)$_2$+10 g SrHPO$_4$+5 g SrCO$_3$+10 g K$_2$HPO$_4$
L=3M K$_2$HPO$_4$/1M KH$_2$PO$_4$
L/M=0.22
$C_s$(72 h)=40 MPa

Various modifications and variations of the present invention will be apparent to those skilled in the art without departing from the scope and spirit of the invention. Although the invention has been described in connection with specific preferred embodiments, it should be understood that the invention as claimed should not be unduly limited to to such specific embodiments. Indeed, various modifications of the described modes for carrying out the invention which are obvious to those skilled in the art are intended to be within the scope of the claims. All publications, patents and patent applications cited in this specification are herein incoporated by reference in their entirety.

What is claimed is:

1. A composition comprising:
   a) a water-combinable combination of a calcium phosphate and a strontium phosphate, wherein a molar ratio of calcium to phosphate is about 1 to about 1.5, and a molar ratio of strontium to phosphate is not greater than about 1.5; and
   b) a salt of phosphoric acid, wherein said composition does not contain magnesium ions or contains no more than trace amounts of magnesium ions.

2. The composition of claim 1, wherein said phosphate is orthophosphate.

3. The composition of claim 2, wherein said calcium, strontium and orthophosphate comprise a powder mixture.

4. The composition of claim 2, wherein said phosphoric acid is orthophosphoric acid.

5. The composition of claim 4, wherein said salt is selected from the group consisting of an alkali salt and an ammonium salt.

6. The composition of claim 5, wherein the alkali salt of the orthophosphoric acid comprises at least one of sodium- (Na-) and potassium-(K-) salt.

7. The composition of claim 6, wherein the alkali salt of the orthophosphoric acid is selected from the group consisting of a primary potassium salt, a secondary potassium salt, a primary sodium salt, a secondary sodium salt, and combinations of said potassium and sodium salts.

8. The composition of claim 5, wherein the alkali or ammonium salt of the orthophosphoric acid is present in an aqueous solution.

9. The composition of claim 1, wherein said trace amounts of magnesium ions are of insufficient quantity to substantially inhibit the formation of a strontium-apatite structure.

10. The composition of claim 1, further comprising an aqueous solution having a pH value in the range of about 5 to about 12.

11. The composition of claim 1, wherein the strontium is present in a powder mixture as strontium phosphate or strontium hydrogenphosphate, or a mixture thereof.

12. The composition of claim 11, wherein the strontium phosphate, the strontium hydrogenphosphate, or the mixture thereof is present in said powder mixture in an amount of more than about 10 wt.-% to about 60 wt.-%.

13. The composition of claim 11, wherein the powder mixture additionally contains strontium carbonate.

14. A composition comprising:
   a) a water-combinable powder mixture of calcium, strontium and orthophosphate, wherein a molar ratio of calcium to phosphate is about 1 to about 1.5, and a molar ratio of strontium to orthophosphate is not greater than about 1.5, wherein the powder mixture comprises $Ca_3(PO_4)_2$ (TCP) and at least one of $SrHPO_4$ and $Sr_3(PO_4)_2$; and
   b) a salt of phosphoric acid, wherein said composition does not contain magnesium ions or contains no more than trace amounts of magnesium ions.

15. The composition of claim 14, wherein the powder mixture further comprises at least one of $NaH_2PO_4$, $Na_2HPO_4$, $KH_2PO_4$, $K_2HPO_4$, $SrCO_3$ and combinations of Na- and K-salts of orthophosphoric acid.

16. A strontium-apatite cement composition, comprising a powder mixture component and an aqueous component, wherein the powder mixture component contains:
   $Ca_3(PO_4)_2$ (TCP),
   $SrHPO_4$ and/or $Sr_3(PO_4)_2$, and
   $SrCO_3$; and
   wherein the aqueous component contains a solution of an alkali salt or an ammonium salt of orthophosphoric acid.

17. The strontium-apatite cement composition of claim 16, wherein the aqueous component comprises a solution of $(NH_4)_2HPO_4$.

18. The strontium-apatite cement composition of claim 16, wherein the aqueous component comprises a solution of primary and/or secondary Na- and/or K-salts of the orthophosphoric acid.

19. The strontium-apatite cement composition of claim 16, wherein the aqueous component is selected from the group consisting of a solution of the primary salt $NaH_2PO_4$ and/or $KH_2PO_4$; a solution of the secondary salt $K_2HPO_4$ and/or $Na_2HPO_4$; and a solution of a mixture of the primary salt $KH_2PO_4$ and/or $NaH_2PO_4$ with the secondary salt $K_2HPO_4$ and/or $Na_2HPO_4$.

20. The strontium-apatite cement composition of claim 16, wherein the powder mixture additionally contains $NaH_2PO_4$ and/or $Na_2HPO_4$; $KH_2PO_4$ and/or $K_2HPO_4$; or combinations of Na- and K-salts of said orthophosphoric acid.

21. The strontium-apatite cement composition of claim 16, wherein $SrHPO_4$ and/or $Sr_3(PO_4)_2$ is present in the powder mixture component in an amount in the range from about 10 wt.-% to about 60 wt.-%.

22. The strontium-apatite cement composition of claim 16, wherein $SrCO_3$ in the powder mixture component is present in an amount in the range from about 0.01 wt.-% to about 10 wt.-%.

23. A composition according to claim 16, wherein at least one of the powder component and the aqueous component contains a pharmacologically and/or biologically active substance.

24. A composition according to claim 23, wherein the pharmacologically and/or biologically active substance is selected from the group consisting of an antibiotic, a cytostatic agent, an analgetic agent, a disinfectant, a growth factor, a protein and a biopolymer.

25. A composition according to claim 23, wherein the pharmacologically and/or biologically active substance is selected from the group consisting of gentamicin, tobramycin, clindamycin, vancomycin, a substance of the TGF-β- series and a substance of the BMPs series.

26. A composition according to claim 16, wherein the powder mixture component additionally contains a substance in the form of granular particles, which dissolves in the aqueous component.

27. A method for augmenting bone, comprising delivering a preparation according to claim 1 to a bone site.

28. A method for augmenting bone, comprising delivering a preparation according to claim 16 to a bone site.

29. A process for preparing a strontium-apatite cement, comprising the steps of:
   mixing a powder mixture component and an aqueous component, as set forth in claim 16 to produce a paste; and
   allowing the paste to harden during formation of strontium-apatite as reaction product to produce said strontium-apatite cement.

30. The process according to claim 29, wherein said paste is filled into a mold to produce defined molded bodies.

31. The process according to claim 29, wherein an injectable liquid is formed after the mixing and before the hardening of the paste.

* * * * *